US005648059A

United States Patent [19]
Gray et al.

[11] Patent Number: 5,648,059
[45] Date of Patent: *Jul. 15, 1997

[54] METHODS FOR REDUCING NON-TARGET RETENTION OF IMMUNOCONJUGATES AND METABOLITES THEREOF

[75] Inventors: Mary Ann Gray, Seattle; Don Axworthy, Brier, both of Wash.; David Wilkening, Midland, Mich.

[73] Assignee: NeoRx Corporation, Seattle, Wash.

[*] Notice: The term of this patent shall not extend beyond the expiration date of Pat. No. 5,380,513.

[21] Appl. No.: 337,477

[22] Filed: Nov. 8, 1994

Related U.S. Application Data

[62] Division of Ser. No. 933,608, Aug. 21, 1992, Pat. No. 5,380,513, which is a continuation of Ser. No. 415,055, Sep. 29, 1989, abandoned.

[51] Int. Cl.⁶ .................................................. A61K 39/395
[52] U.S. Cl. ................... 424/1.49; 424/1.53; 424/9.341; 424/178.1; 424/182.1; 424/9.4; 424/9.1
[58] Field of Search ............................... 424/1.49, 1.53, 424/9, 178.1, 182.1

[56] References Cited

U.S. PATENT DOCUMENTS

| | | | |
|---|---|---|---|
| 4,624,846 | 11/1986 | Goldenberg | 424/1.1 |
| 4,731,244 | 3/1988 | Talle et al. | 424/85.8 |
| 4,946,675 | 8/1990 | Baldwin et al. | 424/85.91 |
| 5,034,223 | 7/1991 | Abrams et al. | 424/85.8 |
| 5,171,563 | 12/1992 | Abrams et al. | 424/1.1 |
| 5,380,513 | 1/1995 | Gray et al. | 424/1.49 |

FOREIGN PATENT DOCUMENTS

| | | |
|---|---|---|
| 0308208 | 3/1989 | European Pat. Off. . |
| 8809182 | 12/1988 | WIPO . |

OTHER PUBLICATIONS

Halpern et al., "Reducing Renal (R) Uptake of 111In FAB: Effect of FAB Mass," abstract describing Poster Session No. 664, p. 714, *Journal of Nuclear Medicine*.

Bernard et al., The Renal Uptake of Proteins: "A Non-selective Process in Conscious Rats," *Kidney International*, 34;175–185 (1988).

Morgensen et al., "Studies on Renal Tubular Protein Reabsorption: Partial and Near Complete Inhibition of Certain Amino Acids," *Scand. J. Clin. Lab. Invest.*, 37:477–486 (1977).

Sumpio et al., "Kinetics, Competition, and Selectivity of Tubular Absorption of Proteins," pp. F379–F392 *American Physiological Society* (1982).

Dorland's Illustrated *Medical Dictionary* 267th ed pp. 6 and 1125.

*Primary Examiner*—Ponnathapura Achutamurthy
*Attorney, Agent, or Firm*—Burns, Doane, Swecker & Mathis

[57] ABSTRACT

Methods for reducing non-target retention of active moieties associated with immunoconjugates and their metabolites, and more specifically, for reducing renal retention of such active moieties, are disclosed. Methods of the present invention comprise administering an effective amount of a non-target reduction moiety, such as lysine, in addition to a therapeutically or diagnostically effective amount of an immunoconjugate. The non-target reduction moiety localizes in the kidneys and inhibits renal retention and reabsorption of active moieties associated with immunoconjugates and their metabolites.

18 Claims, No Drawings

METHODS FOR REDUCING NON-TARGET RETENTION OF IMMUNOCONJUGATES AND METABOLITES THEREOF

This application is a divisional of application Ser. No. 07/933,608, filed Aug. 21, 1992, now U.S. Pat. No. 5,380,513, which is a File Wrapper Continuation application of Ser. No. 07/415,055 filed on Sep. 29, 1989, abandoned.

TECHNICAL FIELD

The present invention relates generally to methods for reducing non-target retention of immunoconjugates and their metabolites and relates more specifically to reducing renal retention of active moieties associated with immunoconjugates and metabolites. Reduced retention of immunoconjugates and metabolites at non-target sites increases the dosage permitted for therapeutic or diagnostic purposes, increases diagnostic imaging clarity, and reduces damage to non-target cells and/or tissue(s).

BACKGROUND ART

Agents that are effective in killing neoplastic and other diseased or abnormal cells generally cannot be administered to a patient in effective doses because they also exert cytotoxic effects on normal cells. Therapeutic protocols for treating cancer and other disorders using cytotoxic agents such as toxins, drugs, radioisotopes, and the like are generally limited by the toxicity of the cytotoxic agent to normal cells and tissues. Efforts have therefore been directed to linking cytotoxic therapeutic agents to targeting agents, such as antibodies, which are capable of localizing at certain target cells and tissue(s).

Research efforts in the field of tumor immunology have identified antibodies to antigenic determinants expressed preferentially on tumor cells. Such antibodies, and fragments thereof, may be employed as carriers for cytotoxic agents to provide selective delivery of cytotoxic agents to target tissues. Antibodies, fragments thereof, and the like have also been utilized as carriers for diagnostic agents such as diagnostic radioisotopes to provide selective delivery of the diagnostic agent to target tissues, thereby providing enhanced diagnostic imaging properties. Diagnostic and therapeutic immunoconjugates comprising an active moiety exhibiting diagnostic or therapeutic properties and a targeting moiety exhibiting specificity and affinity for target cells, tissue(s), antigens, or the like, are believed to be of tremendous potential in diagnosis and treatment of cancer and a variety of other diseases. Development of techniques for generating monoclonal antibodies having specificity for a single epitope has further expanded the potential for immunoconjugates as in vivo diagnostic and therapeutic agents.

Most antibodies capable of localizing at human tumors have some normal tissue cross-reactivity. In general, cross-reactive binding is characterized as binding of an antibody binding site at an epitope recognized by the antibody on non-target cells expressing the epitope. These cross-reactive sites may preferentially bind injected immunoconjugates or metabolites thereof. Cross-reactive, non-target binding may divert a substantial portion of the administered dose from the target site(s), especially if the cross-reactive, non-target sites are concentrated in well-perfused organs. Reducing cross-reactive binding of the antibody or conjugates to non-target cells without adversely affecting their tumor localization would be advantageous.

Nonspecific binding of an antibody or fragment or conjugate thereof generally occurs through mechanisms other than the antigen-recognition binding site on the antibody. For example, antibody may be bound to non-target sites in the liver and spleen when its $F_c$ receptors bind to cells in these non-target organs. Like cross-reactive binding, non-specific binding may substantially reduce the target:nontarget ratio of immunoconjugate protocols, and reducing non-specific binding of conjugates or metabolites thereof to non-target cells without adversely affecting their tumor localization would be advantageous.

Localization of specific antibodies, fragments, immunoconjugates and metabolites thereof at non-target sites due to nonspecific and cross-reactive binding has generally been dealt with, if at all, by co-administering relatively large doses of specific, unconjugated antibody. U.S. patent application No. 06/917,176, filed Oct. 9, 1986, now abandoned, teaches a method for enhanced delivery of immunoconjugates to target cells comprising administering an adequate dosage of blocking antibodies or fragments capable of nonspecific and/or cross-reactive binding to non-target cells, in addition to an effective dosage of immunoconjugates comprising antibodies or fragments specific for the target cells. Irrelevant antibodies may be used to reduce nonspecific and cross-reactive binding of specific antibodies, and unconjugated specific antibody may be used to bind cross-reactive sites prior to the administration of the conjugated specific antibody.

Antibody fragments are frequently used as the targeting moiety for immunoconjugates. Experimental evidence has suggested that immunoconjugates comprising antibody fragments accumulate at target sites such as tumor sites more rapidly than immunoconjugates comprising their whole antibody counterparts. More rapid target site accumulation may be due to the smaller size of the targeting moiety, since decreased immunoconjugate size generally facilitates egress across the blood vessel and capillary walls into the tumor bed. Antibody fragments have shorter serum half-lives than the corresponding whole antibody, however, and a relatively large percentage of the immunoconjugates comprising antibody fragments may be cleared from circulation prior to tumor localization, despite the increased tumor localization capability of the fragments.

Reduction of immunogenicity is yet another important factor in immunoconjugate development efforts. Where the targeting moiety of the immunoconjugate is derived from a species different from that of the patient, the likelihood of stimulating antiglobulin production in the patient, particularly after repeated diagnostic and/or therapeutic treatments, is quite high. In efforts to reduce immunogenicity, antibody fragments, including various constituents of the antibody variable regions, have been used to quantitatively reduce the amount of antibody present. Use of antibody fragments as targeting moieties in immunoconjugates introduces other problems, however, such as reduced serum half-life and more rapid clearance.

SUMMARY OF THE INVENTION

The present invention is directed generally to methods for reducing non-target retention of immunoconjugates and metabolites thereof and is directed more specifically to methods for reducing renal retention of active moieties associated with immunoconjugates and their metabolites. One problem associated with the administration of immunoconjugates comprising antibody fragments such as Fab or Fv, is the tendency for the active moieties, e.g., radionuclides, to localize in the kidneys. Additionally, metabolites of immunoconjugates comprising whole antibodies or larger antibody fragments, such as F(ab')$_2$ fragments, may localize in the kidneys. In general, substances (such as active moieties) associated with a proteinaceous moiety and having a molecular weight of less than about 50,000 to 60,000 accumulate in the kidneys and are filtered as glomerular filtrate. Immunoconjugates comprising active moieties linked to Fab and Fv fragments in the kidneys are generally processed in the glomerular filtrate. Additionally, immunoconjugates comprising whole antibody and F(ab')$_2$ targeting moieties may be catabolized after in vivo administration to form Fab' or smaller proteinaceous fragments bound to active moieties, which may also accumulate in the kidneys and be processed in the glomerular filtrate.

Relatively low molecular weight materials associated with proteinaceous moieties, such as immunoconjugates and metabolites thereof, which are processed in the glomerular filtrate are subsequently reabsorbed and returned to the bloodstream via peritubular capillaries. Localization, retention and reabsorption of active moieties of immunoconjugates and metabolites in the kidneys reduces the target:non-target ratio of the immunoconjugate and has several undesirable effects. When diagnostic immunoconjugates are being administered, increased non-target retention reduces the amount of diagnostic imaging agent concentrated in target areas, and thus reduces imaging intensity and clarity. Furthermore, localization and reabsorption of the radioactive imaging agent in the kidneys may damage normal tissue, and it may mask target sites in proximity to the kidneys. When therapeutic immunoconjugates are being administered, renal retention and reabsorption of immunoconjugates and their metabolites causes undesirable renal toxicity, thereby lowering the therapeutic index of the immunoconjugate. In many cases, the kidney may be the limiting organ of toxicity, preventing administration of larger, more efficacious doses of immunoconjugates.

Methods of the present invention comprise administering an effective amount of a non-target reduction moiety, in addition to a therapeutically or diagnostically effective amount of an immunoconjugate. According to preferred embodiments of the methods of the present invention, the non-target reduction moiety localizes in the kidneys and inhibits retention and reabsorption of active moieties associated with immunoconjugates and their metabolites. As a result of the physiological effect of the non-target reduction moiety, active moieties associated with immunoconjugates and their metabolites are not reabsorbed, but are removed from the non-target kidney sites by urinary excretion.

Lysine is a preferred non-target reduction moiety for reducing non-target retention of active moieties associated with immunoconjugates and their metabolites in the kidneys according to methods of the present invention. Lysine inhibits tubular reabsorption of immunoconjugates and metabolites comprising a proteinaceous moiety, and thereby promotes urinary excretion of metabolites comprising active moieties localized at non-target kidney sites. Lysine may be administered prior to, and/or simultaneously with, and/or subsequently to diagnostic and/or therapeutic immunoconjugates to provide reduced non-target localization of active moieties associated with immunoconjugates and their metabolites.

DETAILED DESCRIPTION OF THE INVENTION

"Immunoconjugates" employed in the methods of the present invention comprise a diagnostically or therapeutically active moiety (the "active moiety") bound to and/or associated with a targeting moiety. An "effective amount" of an immunoconjugate is an amount sufficient to exert a diagnostic or therapeutic effect. For example, a diagnostically effective amount of a diagnostic radiolabeled imaging immunoconjugate is an amount sufficient to produce a detectable scintigraphic image at a target site. Likewise, a therapeutically effective amount of a therapeutic immunoconjugate is an amount sufficient to produce cellular damage or destruction at a target site.

"Non-target reduction moieties" employed in the methods of the present invention include moieties which are capable of localizing at non-target cells or tissue(s) of interest and saturating and/or blocking a physiological pathway which would otherwise result in retention of active moieties associated with immunoconjugates and metabolites, or exerting a physiological effect which inhibits retention of active moieties associated with immunoconjugates and metabolites. For example, preferred non-target reduction moieties inhibit tubular renal reabsorption of immunoconjugates and/ or immunoconjugate metabolites having an active moiety associated with a proteinaceous moiety. "Proteinaceous moiety" means a moiety comprising an amino acid or functional constituent or derivative thereof, polypeptide, or the like. An "effective" dose of a non-target reduction moiety is a dose which reduces retention of immunoconjugates and/or their metabolites at a non-target site by at least about 20%.

Physiological characteristics of the diagnostic and/or therapeutic immunoconjugates administered and the metabolites formed therefrom determine, at least in part, the biodistribution and target:non-target ratios of the immunoconjugates. Such physiological characteristics include factors such as metabolism and catabolism of the conjugates (i.e., what metabolites are formed as well as where such metabolites are formed within the patient) and clearance rate and retention characteristics of the metabolites (i.e., what are the properties of the formed metabolites). Different targeting moieties may be more or less likely to localize at non-target sites due to cross-reactive and nonspecific binding, or other factors. Similarly, immunoconjugates and metabolites thereof comprising antibody fragments may be more prone to localize at certain non-target sites than those comprising whole antibody.

Immunoconjugates comprising Fab and Fv fragments as targeting moieties wherein the active moiety is relatively small, i.e., the molecular weight of the immunoconjugate is less than about 50,000 to 60,000, may be filtered in the kidneys as intact immunoconjugates. Many of these intact immunoconjugates will subsequently be reabsorbed, since they are primarily proteinaceous in character, and tubular reabsorption mechanisms preferentially reabsorb proteinaceous moieties. Immunoconjugates comprising whole antibodies or larger antibody fragments, such as F(ab')$_2$, are not typically filtered and reabsorbed in the kidneys, since they are too large. Smaller metabolites of immunoconjugates comprising whole antibodies or larger antibody fragments comprising an active moiety associated with a proteinaceous moiety may, however, localize in the kidneys and be filtered and reabsorbed. Similarly, immunoconjugates comprising Fab and Fv fragments may be metabolized in vivo to form smaller metabolites comprising an active moiety associated with a proteinaceous moiety.

Active moieties are frequently linked to proteinaceous targeting moieties using lysine residues of the antibody or fragment. Lysine residues have a terminal amine group which may be reacted with an activated ester on the active moiety or on a linking agent such as a heterobifunctional reagent to provide an amide bond linkage. It has been hypothesized that catabolism of immunoconjugates in vivo may result in the lysine residue bound to the active agent being cleaved from the remainder of the targeting moiety. Such immunoconjugate metabolites would thus comprise an active moiety such as a diagnostic or therapeutic radionuclide metal chelate, or a drug or small toxin, linked directly or indirectly to a lysine residue. These relatively low molecular weight metabolites may localize in the kidneys, and their size and association with a proteinaceous moiety would promote filtration and absorption of the metabolites. Immunoconjugates may also be catabolized in vivo to yield active moieties linked directly or indirectly to proteinaceous fragments other than or in addition to lysine residues.

Preferred non-target reduction moieties employed in the methods of the present invention include lysine and functional constituents or derivatives thereof. Other substances such as ornithine, arginine, epsilon amino caproic acid, cyclocaprone, and the like, would also be suitable for use as non-target reduction moieties. Lysine is the preferred non-target reduction moiety for use in the present invention. In general, amino acids and other substances having a free amino group with a pKa similar to that of lysine are suitable non-target reduction moieties for use in the methods of the present invention.

The non-target reduction moiety may be administered prior to and/or substantially simultaneously with and/or following administration of the diagnostic or therapeutic immunoconjugate. According to preferred methods of the present invention, the non-target reduction moiety is administered prior to administration of the diagnostic or therapeutic immunoconjugate so that the non-target reduction moiety has an opportunity to localize and exert its physiological effect at the non-target site prior to localization of the immunoconjugate and metabolites at the non-target site(s). The non-target reduction moiety is also preferably administered continuously or at intervals after administration of the immunoconjugate to maintain and/or prolong the physiological effect at the non-target site(s). For example, one preferred regimen is to administer an effective dose of the non-target reduction moiety continuously for a time period of from about 5 minutes to about one hour prior to administration of immunoconjugates, and to continue administration of non-target reduction moieties for several hours after administration of immunoconjugates. Another preferred regimen is to administer an effective dose of the non-target retention moiety about five minutes to about one hour prior to administration of the immunoconjugates, and to administer effective doses of the non-target retention moiety at intervals of about 20 minutes to about 2 hours after administration of the immunoconjugates and for a period of from about 4 hours to about 20 hours. The non-target reduction moiety may be administered orally, intravenously, intraperitoneally, or the like. Additionally, the non-target organ of interest may be perfused with a the non-target solution containing reduction moiety.

Immunoconjugates administered according to methods of the present invention comprise targeting moieties linked to or otherwise associated with active moieties. Targeting moieties provide selective delivery of an active moiety to a receptor, substrate, cell surface membrane, antigenic determinant, or other site in proximity to the target cells or tissue(s). Suitable targeting moieties for use in immunoconjugates of the present invention include proteinaceous substances having protein or polypeptide moieties, and which may include carbohydrate moieties such as polysaccharides, glycoproteins, or other compounds having a carbohydrate moiety. Preferred proteinaceous targeting agents include antibodies (polyclonal and monoclonal), receptors (particularly cell surface receptors such as lectins), enzymes (e.g., fibrinolytic enzymes), biologic response modifiers (e.g., interleukins, interferons, lymphokines, erythropoietin, growth factors, colony stimulating factors, and the like), peptide hormones, and fragments thereof. Microaggregated proteins, such as microaggregated albumin (MAA) and the like, may also be used as targeting moieties.

Monoclonal antibodies or fragments thereof are especially preferred proteinaceous targeting moieties. The specific monoclonal antibody chosen for in vivo administration in connection with a diagnostic or therapeutic protocol will target cells relevant to the patient's physiological condition. Among the many such monoclonal antibodies that may be used are anti-TAC, or other interleukin-2 receptor antibodies; 9.2.27 and NRML-05 to the 250 kilo-dalton human melanoma-associated proteoglycan; NRLU-10 to 37–40 kilodalton pancarcinoma glycoprotein; NRCO-02 having colon specificity; and OVB-3 to an as yet unidentified tumor-associated antigen. Numerous antibodies which are known or have not yet been isolated are also suitable for use in the present invention. Antibodies derived from hybridomas or by means of genetic or protein engineering techniques may be employed.

The targeting moieties may be modified as desired, as long as the targeting capability is retained. For example, chimeric antibodies which are produced by recombinant DNA techniques and have specificity determining portions derived from non-human sources and other portions derived from human sources, may be conjugated to active moieties to provide conjugates useful according to the present invention. Antibodies employed in the present invention may comprise intact molecules, fragments thereof, or functional equivalents thereof. Exemplary antibody fragments include F(ab')$_2$, Fab' Fab, and Fv fragments, which may be produced by conventional methods, or by genetic or protein engineering techniques. Engineered antibodies referred to as single chain antibodies may also be used. Proteinaceous targeting moieties may also undergo chemical modification to effect a shift in the isoelectric point of the resulting "charge modified" protein, as described in co-pending U.S. patent application Mp/07/157,273, entitled "Alteration of Pharmacokinetics of Proteins by Charge Modification".

When used as delivery vehicles for diagnostic or therapeutic active moieties, the targeting moiety may be associated with the active moiety by any convenient method. The active moiety may be bound directly to the targeting moiety, or it may be bound indirectly via an intermediary molecule such as a chelate, a small molecule linker, a carrier molecule, or the like. Numerous linking technologies are known in the art for binding diagnostically and therapeutically active moieties to targeting moieties. Linking methodologies described below are illustrative only, and many known technologies may be used.

The method of the present invention is suitable for use with immunoconjugates having an active moiety of a size and character promoting renal localization, filtration and reabsorption if linked to a proteinaceous or carbohydrate moiety. Practically speaking, immunoconjugates useful in the methods of the present invention comprise active moieties (one or multiple) having molecular weights of less than about 50,000 to 60,000. Active moieties suitable for use in the present invention include, generally, diagnostic moieties such as diagnostic radionuclides, and therapeutic moieties such as toxins, toxin fragments, therapeutically effective drugs, biologic response modifiers, and therapeutic radionuclides.

Therapeutic and/or diagnostic radionuclides which may be employed as active moieties according to the present invention include alpha-emitters, beta-emitters, gamma-emitters, positron-emitters, X-ray emitters, fluorescence-emitters, or the like. Suitable diagnostic radionuclides which are preferred for use in the present invention include $^{99m}$Tc, $^{97}$Ru, $^{111}$In, $^{113}$In, $^{123}$I, $^{76}$Br, $^{203}$Pb, $^{18}$F, and $^{64}$Cu; nuclear magnetic resonance imaging contrast agents, X-ray contrast agents; and other diagnostic imaging agents. These diagnostic agents are detectable by external, non-invasive means, using conventional gamma camera instrumentation. $^{99m}$Tc is an especially preferred diagnostic radionuclide imaging agent. Beta- or alpha-emitters are preferred for therapeutic applications. Therapeutic radionuclides suitable for use in immunoconjugates administered according to methods of the present invention include, among others, $^{188}$Re, $^{186}$Re, $^{212}$Pb, $^{212}$Bi, $^{109}$Pd, $^{67}$Cu, $^{125}$I, $^{131}$I, $^{90}$Y, $^{67}$Cu, $^{211}$At, $^{105}$Rh, $^{198}$Au, $^{199}$Au, and $^{77}$Br, $^{186}$Re and $^{131}$I are especially preferred therapeutic radionuclides.

Metal radionuclides, whether diagnostic or therapeutic, are preferably provided in the form of a stable complex such as a radionuclide metal chelate, which may be prepared by known methods. Diagnostic $^{99m}$Tc and therapeutic rhenium radionuclides are typically introduced into a chelating agent to form a stable radionuclide metal chelate, and the radionuclide metal chelate is conjugated to a targeting moiety such as an antibody or fragment. Metal chelating agents having nitrogen and sulfur donor atoms, such as dithiodiaminocarboxylic acids and dithiodiamidocarboxylic acids (known as N$_2$S$_2$ chelating agents), and thiotriaza chelating compounds (known as N$_3$S chelating agents), are preferred. Chelating compounds having the following general formulas are preferred:

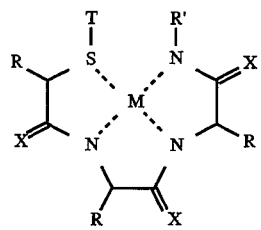

wherein:

T is H or a sulfur protecting group;

each X independently represents H$_2$ or O;

M is a radionuclide ion, to which 1 or 2 oxygen atoms may be bonded;

each R independently represents a substituent selected from the group consisting of hydrogen; alkyl; geminal dialkyl; a non-alkyl side chain of an amino acid other than cysteine (alkyl side chains being covered when R is an alkyl group); and —(CH$_2$)$_n$—Z;

Z represents —COOH, a conjugation group, or a targeting compound;

n is an integer of from 1 to about 4;

R' is H$_2$; —(CH$_2$)$_n$—Z; or an alkyl group having one or more polar groups substituted thereon; and the compound comprises at least one —(CH$_2$)$_n$—Z substituent wherein Z is a conjugation group or a targeting compound.

Suitable metal chelating agents are disclosed in European Patent Application Publication Nos. 0 188 256 and 0 284 071, as well as U.S. patent application No. 07/367,502 filed Jun. 16, 1989, which are incorporated by reference herein in their entireties. Other metal chelating agents which are known in the art are also suitable for use in the radionuclide compositions of the present invention.

The conjugation group is a functional group which reacts with a group on the desired targeting moiety to bind the radionuclide metal chelate to the targeting agent. Proteinaceous targeting moieties contain a variety of functional groups such as carboxylic acid (COOH) or free amine (—NH$_2$) groups, which are available for reaction with a suitable conjugation group on a chelating agent. For example, an active ester on the chelating agent reacts with free amine groups on lysine residues of proteins to form amide bonds. Alternatively, the protein and/or chelating agent may be derivatized to expose or attach additional reactive functional groups. The derivatization may involve attachment of any of a number of linker molecules. Alternatively, the derivatization may involve chemical treatment of the protein to generate, for example, free sulfhydryl groups which are reactive with maleimide conjugation groups on a chelating agent.

Among the preferred conjugation groups for reaction with proteinaceous targeting agents are esters. The esters which may be utilized as conjugation groups represented by "Z" are those esters which provide a covalent, amide linkage with a polypeptide in an aqueous medium. One or another of the reactive esters may be preferred, depending upon the particular radionuclide, the protein, and the conditions for conjugation, as is understood in the art of peptide chemistry. Common esters which find use are o- and p- nitrophenyl, 2-chloro-4-nitrophenyl, cyanomethyl, 2-mercaptopyridyl, hydroxybenztriazol, N-hydroxy succinimide, trichlorophenyl, tetrafluorophenyl, thiophenyl, tetrafluorothiophenyl, o-nitro-p-sulfophenyl, N-hydroxy phthalimide, and the like.

Alternatively, when the targeting agent has a carbohydrate moiety, derivatization may involve chemical treatment of the carbohydrate, such as glycol cleavage of the sugar moiety of a glycoprotein antibody with periodate to generate free aldehyde groups. The free aldehyde groups on the antibody mat be reacted with free amine or hydrazine conjugation groups on the chelating agent to bind the radionuclide metal chelate thereto.

Another type of binding molecule which may be used to conjugate a radionuclide such as $^{131}$I to a targeting moiety is a small linker molecule to which a radionuclide may be stably bound by a single covalent bond. Radiohalogenated small molecules for binding to proteinaceous targeting agents are described in European Patent Application Nos. 0 203 764 and 0 289 187, which are incorporated herein by reference in their entireties. Alternatively, many active moieties may be linked to other active and/or targeting moieties directly or through the use of carriers, as is well known in the art.

Toxins which may be employed as active moieties in immunoconjugates for use in methods of the present invention include ribosomal inactivating proteins, mycotoxins such as trichothecenes and other toxins having molecular weights of less than about 50,000 to 60,000. Immunoconjugates comprising trichothecenes are disclosed in U.S. Pat. No. 4,744,981, the teachings of which are incorporated herein by reference in their entirety. Therapeutically effective modified toxins or fragments thereof, such as those produced by means of genetic engineering or protein engineering techniques may also be used.

Various drugs may also be employed as therapeutically active moieties, depending on the nature of the patient's illness. Many cytotoxic or antineoplastic drugs that have been used to treat various forms of cancer are suitable for use in the present invention, including nitrogen mustards such as L-phenylalanine nitrogen mustard and cyclophosphamide; intercalating agents such as cis diamino dichloro platinum; antimetabolites such as 5-fluorouracil, porphyrin and related compounds; vinca alkaloids such as vincristine and vinblastine; antibiotics such as adriamycin and bleomycin. Other specific chemotherapeutic agents which may be employed as active moieties include methotrexate; aminopterin; vindesine; blenoxane; hematoporphyrin derivative; dihematoporphyrin ether; mitamycin; mithramycine; chlorambucil; pyrimidine analogs, such as fluorouracil and deoxyuridine; purine analogs, such as thioguanine, mercaptopurine and azathiopurine; cytosine arabinaside; actinomycin D; daunorubicin, doxorubicin, and other anthracycline derivatives; platinum derivatives, and the like. These and other suitable chemotherapeutic agents are well known in the art, and are generally available.

Immunoconjugates comprising toxins, drugs, radionuclide metal chelates, and the like administered according to methods of the present invention, may be coupled using homo- or hetero-bifunctional reagents which are well known in the art to provide thioether, amide bonds or the like. A preferred conjugation methodology for binding active proteinaceous moieties, such as toxins, to proteinaceous targeting moieties generally comprises reacting an active moiety with a heterobifunctional reagent such as succinimidyl 4-(N-maleimidomethyl) cyclohexane-1-carboxylate (SMCC), which has a malemide group at one end and an activated ester group at the other end. The active moiety, generally a protein in this embodiment, is derivatized by nucleophilic attack at the activated ester. The targeting agent, generally an antibody or fragment thereof, is typically treated with a reducing agent such as dithiothereitol (DTT) or the like. Following separation of the derivatized protein from the reaction mixture, a targeting agent which has been treated with a reducing agent to produce a free, native sulfhydryl group, is reacted with the derivatized protein. The targeting moiety is covalently linked to the active moiety by reaction of the sulfhydryl group with the maleimide group to form a conjugate joined by a thioether bond.

Immunoconjugates and non-target reduction moieties are intended for injection into humans or other mammalian hosts according to methods of the present invention. Accordingly, appropriate manufacturing and in vitro storage practices must be observed to provide suitable sterile, pyrogen-free compositions. Although not necessary, it is preferable to use a pharmaceutically acceptable extender or filler to dilute any carrier which might optionally be used, and/or to simplify metering the requisite small quantities of such compounds. Sodium chloride, phosphate-buttered saline (PBS), and glucose solutions are preferred carriers; PBS is especially preferred because it facilitates provision of an isotonic solution. Immunoconjugates and non-target reduction moieties according to the present invention may be diluted as necessary and administered to mammalian hosts orally, intravenously, intraarterially, intraperitoneally, or the like, depending upon a variety of factors known to practitioners in the mammalian diagnostic and therapeutic arts.

Animal studies using non-tumor bearing Balb-C mice were conducted to confirm the efficacy of methods of the present invention by monitoring the biodistribution of diagnostic imaging agents at various time intervals after administration. Biodistribution was measured as the percentage injected dose present in various organs time intervals after administration of the immunoconjugate. Biodistribution data was collected by sacrificing the control or test mice at appropriate time points, removing the organs of interest, and measuring the radioactive level (and thus the retention of radioactive imaging agents) in each of the organs. The following examples are set forth to demonstrate specific examples of the methods of the present invention, and are not intended to limit the invention in any way.

EXAMPLE I

Diagnostic imaging immunoconjugates having the following composition were prepared for in vivo administration: NRML-05(Fab)-$N_2S_2$-$^{99m}$Tc. The targeting moiety was NRML-05(Fab), an antibody fragment capable of binding to the 250 kilodalton human melanoma-associated proteoglycan; the chelating agent was an $N_2S_2$ ligand; and the diagnostically active moiety was $^{99m}$Tc. The specific activity of the preparation was 4.4 µCi/mg, and the purity of the preparation was 96%.

Three control groups of 4 mice each were injected with 100 µl PBS intravenously 5 minutes prior to immunoconjugate administration, and 0.5 ml PBS was administered intraperitoneally at intervals of every (1) 30 minutes thereafter; (2) one hour thereafter; and (3) two hours thereafter. Three test groups of 12 mice each were injected with 100 µl of an aqueous (PBS) lysine solution containing (A) 1 mg lysine; (B) 5 mg lysine; and (C) 10 mg lysine intravenously 5 minutes prior to immunoconjugate administration. In each test group, 4 mice each were subsequently injected with and 0.5 ml lysine solution containing the pre-injection dose of lysine at intervals of every (1) 30 minutes thereafter; (2) one hour thereafter; and (3) two hours thereafter. The biodistribution of immunoconjugates and labeled metabolites was determined four hours post-injection. Results showing kidney uptake as measured by a percentage of the injected dose, were as follows:

| Injection | Percentgae Injected Dose in kidney | | |
|---|---|---|---|
| | 30 min | 1 hour | 2 hours |
| PBS | 2.95% | 3.25% | 3.77% |
| 1 mg lysine | 3.04% | 3.47% | 3.57% |
| 10 mg lysine | 1.91% | 2.46% | 3.32% |
| 20 mg lysine | 1.56% | 1.97% | 3.03% |

The results indicate that higher doses of lysine as a non-target reduction moiety produce improved results, i.e., the percentage of the injected dose detected in the kidney is decreased. Additionally, more frequent injections of the non-target reduction moiety after the immunoconjugate administration are beneficial and result in substantially reduced kidney retention compared to less frequent injection intervals.

EXAMPLE II

Diagnostic imaging immunoconjugates having the following composition were prepared for in vivo administration: NRLU-10(Fab)-$N_3S$-$^{99m}$Tc. The targeting moiety was NRLU-10(Fab), an antibody fragment capable of binding to the 37–40 kilodalton pancarcinoma glycoprotein; the chelating agent was an $N_3S$ ligand; and the diagnostically active moiety was $^{99m}$Tc. The specific activity of the preparation was 11 µCi/mg, and the purity of the preparation was 99%.

A control group of 20 mice was injected with 100 µl phosphate buffered saline (PBS) intravenously 5 minutes prior to immunoconjugate administration, and 0.5 ml PBS was administered intraperitoneally every 30 minutes thereafter. The test group of 20 mice was injected with 100 µl of an aqueous (PBS) lysine solution containing 10 mg lysine intravenously 5 minutes prior to immunoconjugate administration, and 0.5 ml lysine solution containing 10 mg lysine was administered intraperitoneally every 30 minutes thereafter. The biodistribution of immunoconjugates and labeled metabolites was determined, and the results of kidney uptake, as measured by a percentage of the injected dose, were as follows:

| Time | Kidney Uptake (% of Injected Dose) | | % Retention |
|---|---|---|---|
| (hours) | Control | 10 mg Lysine | Reduction |
| T = 1 | 6.3% | 9.8% | −55.6% |
| T = 2 | 6.5% | 2.2% | +66.2 |
| T = 4 | 4.1% | 1.5% | +63.4 |
| T = 6 | 3.1% | 1.0% | +67.7 |
| T = 20 | .85% | .50% | +41.2 |

EXAMPLE III

Diagnostic imaging immunoconjugates having the following composition were prepared for in vivo administration: NRLU-10(Fab)-$N_3S$-$^{99m}$Tc. The targeting moiety was NRLU-10(Fab); the chelating agent was an $N_3S$ ligand; and the diagnostically active moiety was $^{99m}$Tc. The specific activity of the preparation was 6.5 µCi/mg and the purity of the preparation was 98.8%.

A control group of 20 mice was injected with 100 µl PBS intravenously 5 minutes prior to immunoconjugate administration, and 0.5 ml PBS was administered intraperitoneally every hour thereafter. The test group of 20 mice was injected with 100 µl of an aqueous (PBS) lysine solution containing 10 mg lysine intravenously 5 minutes prior to immunoconjugate administration, and 0.5 ml lysine solution containing 10 mg lysine was administered intraperitoneally every hour thereafter. The biodistribution of immunoconjugates and labeled metabolites was determined, and the results of kidney uptake, as measured by a percentage of the injected dose, were as follows:

| Time | Kidney Uptake (% of Injected Dose) | | % Retention |
|---|---|---|---|
| (hours) | Control | 10 mg Lysine | Reduction |
| T = 1 | 12.2% | 9.3% | −23.8% |
| T = 2 | 8.1% | 4.5% | +44.4 |
| T = 4 | 5.2% | 2.5% | +51.9 |
| T = 20 | 1.2% | 0.7% | +41.7 |

While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic preinciples of the invention.

What is claimed is:

1. An improved method of therapeutic treatment of a mammalian subject comprising the administration of a therapeutically effective amount of a therapeutic immunoconjugate wherein the improvement comprises;

additionally administering to said mammalian subject at least one urinary excretion promoting agent which localizes at renal sites and inhibits the retention and reabsorption of said therapeutic immunoconjugate and/ or metabolites thereof in the bloodstream of said mammalian subject wherein said at least one urinary excretion promoting agent is administered in an amount effective to reduce non-target retention of active moieties contained in said therapeutic immunoconjugate or metabolites thereof at non-targeted renal sites.

2. An improved method of therapeutic treatment of a mammalian subject comprising the administration of a therapeutically effective amount of a therapeutic-immunoconjugate wherein the improvement comprises;

additionally administering to said mammalian subject at least one urinary excretion promoting agent which localizes at renal sites not targeted by said therapeutic immunoconjugate and which inhibits retention and reabsorption of said therapeutic immunoconjugate and/ or metabolites thereof at said non-targeted renal sites wherein said at least one urinary excretion promoting agent is administered in an amount effective to reduce the uptake of said therapeutic immunoconjugate and/or metabolites thereof in the circulating blood of said patient attributable to renal reabsorption of said therapeutic immunoconjugate and/or metabolites thereof.

3. The method of claim 1 or claim 2 wherein the urinary excretion promoting agent comprises lysine.

4. The method of claim 1 or claim 2 wherein the urinary excretion promoting agent is an amino acid or other proteinaceous moiety having a free amino group and having a pKa within the range of pKa's of the group consisting of: ornithine, arginine, epsilon amino caproic acid and tranexamic acid.

5. The method of claim 1 or claim 2 wherein the urinary excretion promoting agent is selected from the group consisting of lysine, ornithine, arginine, epsilon amino caproic acid, tranexamic acid and mixtures thereof.

6. The method of claim 1 or claim 2 wherein the immunoconjugate comprises an antibody or fragment thereof which specifically binds to a target site.

7. The method of claim 1 or claim 2 wherein the immunoconjugate comprises a monoclonal antibody or monoclonal antibody fragment selected from the group consisting of F(ab)', F(ab)'$_2$, Fab and Fv.

8. The method of claim 1 or claim 2 wherein the therapeutic immunoconjugate comprises a therapeutically active moiety selected from the group consisting of radionuclides, drugs, toxins, and biological response modifiers.

9. The method of claim 1 or claim 2 wherein the urinary excretion promoting moiety is administered to the mammalian subject prior to administration of the therapeutic immunoconjugate.

10. The method of claim 1 or claim 2 wherein the urinary excretion promoting moiety is administered about 5 minutes to a about 1 hour prior to administration of said therapeutic immunoconjugate, and at intervals of about 20 minutes to about 2 hours after administration of said immunoconjugate.

11. The method of claim 1 or claim 2 wherein an effective dose of said urinary excretion promoting agent is administered to said mammalian subject continuously for a period from about 5 minutes to about one hour prior to administration of said immunoconjugates to several hours after administration of said immunoconjugates.

12. A composition which is for therapeutic or diagnostic use which comprises:

(i) a therapeutically or diagnostically effective amount of a therapeutic or diagnostic immunoconjugate which comprises a therapeutic or detectable moiety directly or indirectly attached to a targeting moiety; and (ii) an amount of a urinary excretion promoting agent which is effective to reduce the non-target retention of said immunoconujugate or metabolites thereof at non-targeted renal sites and/or to reduce the uptake of said therapeutic or diagnostic immunoconjugate and/or metabolites thereof in the circulating blood of said patient attributable to renal reabsorption of said immunoconjugate and/or metabolites thereof.

13. The composition of claim 12 wherein said urinary excretion promoting agent is selected from the group consisting of lysine, ornithine, arginine, epsilon amino caproic acid, tranexamic and mixtures thereof.

14. The composition of claim 12 wherein the urinary excretion promoting agent comprises lysine.

15. The composition of claim 12 wherein the urinary excretion promoting agent is an amino acid or other proteinaceous moiety containing a free amino group having a pKa within the range of pKa's of the group consisting of: ornithine, arginine, epsilon amino caproic acid and tranexamic acid.

16. The composition of claim 12 wherein the targeting moiety is an antibody or antibody fragment.

17. The composition of claim 12 wherein the therapeutic moiety is selected from the group consisting of radionuclides, drugs, toxins, and biological response modifiers.

18. The composition of claim 12 wherein the detectable moiety is a diagnostic radionuclide.

* * * * *